US006794502B2

(12) United States Patent
Krotz et al.

(10) Patent No.: US 6,794,502 B2
(45) Date of Patent: *Sep. 21, 2004

(54) METHODS FOR REMOVING DIMETHOXYTRITYL GROUPS FROM OLIGONUCLEOTIDES

(75) Inventors: Achim H. Krotz, San Diego, CA (US); Bethany M. McElroy, San Marcos, CA (US); Anthony N. Scozzari, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/103,906

(22) Filed: Mar. 22, 2002

(65) Prior Publication Data

US 2002/0156268 A1 Oct. 24, 2002

Related U.S. Application Data

(63) Continuation of application No. 09/271,220, filed on Mar. 17, 1999, now Pat. No. 6,399,765.

(51) Int. Cl.[7] .................. C07H 21/00; C07H 21/02; C07H 21/04

(52) U.S. Cl. ................. 536/25.31; 536/27.1; 536/27.13

(58) Field of Search ................. 536/25.31, 27.13, 536/27.1

(56) References Cited

U.S. PATENT DOCUMENTS

| | | | |
|---|---|---|---|
| 4,415,732 A | 11/1983 | Caruthers et al. | 536/27 |
| 4,458,066 A | 7/1984 | Caruthers et al. | 536/27 |
| 4,500,707 A | 2/1985 | Caruthers et al. | 536/27 |
| 4,517,338 A | 5/1985 | Urdea et al. | 525/54 |
| 4,668,777 A | 5/1987 | Caruthers et al. | 536/27 |
| 4,725,677 A | 2/1988 | Koster et al. | 536/27 |
| 4,973,679 A | 11/1990 | Caruthers et al. | 536/27 |
| 5,132,418 A | 7/1992 | Caruthers et al. | 536/27 |
| 5,138,045 A | 8/1992 | Cook et al. | 536/27 |
| RE34,069 E | 9/1992 | Koster et al. | 536/27 |
| 5,210,264 A | 5/1993 | Yau | 558/167 |
| 5,218,105 A | 6/1993 | Cook et al. | 536/25.31 |
| 5,459,255 A | 10/1995 | Cook et al. | 536/27.13 |
| 5,539,082 A | 7/1996 | Nielsen et al. | 530/300 |
| 5,571,902 A | 11/1996 | Ravikumar et al. | 536/22.1 |
| 6,399,765 B1 * | 6/2002 | Krotz et al. | 536/25.31 |

FOREIGN PATENT DOCUMENTS

| | | | |
|---|---|---|---|
| EP | 0035255 A1 | 9/1981 | |
| EP | 0035255 | * 9/1981 | C07H/21/00 |
| WO | WO 92/20823 | 11/1992 | |
| WO | WO 96/03417 | * 2/1996 | C07H/21/00 |

OTHER PUBLICATIONS

Alul, R.H. et al., "Oxalyl–CPG: a labile support for synthesis of sensitive oligonucleotide derivatives", *Nucl. Acid Res.*, 1991, 19, 1527–1532.

Barber, I. et al., "Solution–Phase Synthesis of Phosphorothioate Oligodeoxynucleotides by the phosphouiester Method," *Antisense Res. Devel.*, 1995, 5, 39–47.

Beaucage, S.L. et al., "Advances in the Synthesis of Oligonucleotides by the Phosphoramidite Approach", *Tetrahedron.* 1992, 48, 2223–2311.

Bonora, G.M. et al., "Large scale, liquid phase synthesis of oligonucleotides by the phosphoramidite approach," *Nucl. Acids Res.*, 1993, 21 (5), 1213–1217.

Chiang, M.Y. et al., "Antisense Olignucleotides Inhibit Intercellular Adhesion Molecul3 1 Expression by Two Distinct Mechanisms", *J. Biol. Chem.*, 1991, 266, 18162–18171.

Crooke, S.T. et al., "Pharmacokinetic Properties of Several Novel Oligonucleotide Analogs in mice", *J. Pharmacol. Exp. Therapeutics*, 1996, 277, 923–937.

Dahl, O. et al., "Preparation of Nucleoside Phosphorothioates, Phosphorodithioataes and Related Compounds", *Sulfur Reports*, 1991, 11(1), 167–192.

Eck stein, F., "Nucleoside Phosphorothioates", *Ann. Rev. Biochem.*, 1985, 54, 367–402.

Gait, M. J. ed., "An Introduction to Modem Methods of DNA Synthesis," *Oligonucleotide Synthesis, A practical Approach.* IRL Press, Oxford, 1985, IRL Press, Oxford, ch. 1, 1–22.

Gebeyehu, G. et al., "Novel bitinylated nucleotide—analogs for labeling and lolorimetric detection of DNA", *Nucl. Acids Res.* 1987, 15, 4513–4534.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Kornberg, A., *DNA Replication*, W.H. Freeman and Co., San Francisco, 1980, 75–77.

Kresse, J. et al., "The use of S–2–cyanoethyl phosphorothioate in the preparation of oligo 5'–deoxy–5'–thiothymidylates", *Nuc. Acids Res.*, 1975, 2, 1–9.

(List continued on next page.)

Primary Examiner—James O. Wilson
Assistant Examiner—Patrick Lewis
(74) Attorney, Agent, or Firm—Woodcock Washburn LLP

(57) ABSTRACT

The present invention discloses improved methods for oligonucleotide synthesis and purification. In the methods of the invention, a half-life is determined for deprotection of the 5'-OH protecting group at the 5'-terminus of an oligonucleotide post-synthesis. The half-life is used to determine an optimal reaction time for removal of the 5'-OH protecting group. The methods of the invention are amenable to the large-scale synthesis and purification of oligonucleotides.

17 Claims, 2 Drawing Sheets

OTHER PUBLICATIONS

Letsinger, R.L. et al., "Cholesteryl–conjugated oligonucleotides: Synthesis, properties and activity as inhibitors of replication of humbn immunodeficiency virus in cell culture", *Proc. Natl. Acad. Sci.*, 1989, 86, 6553–6556.

Manoharan M. et al., "Oligonucleotide Conjugates: Alteration of the Pharmacokinetic Properties of Antisense Agents", *Nucleosides and Nucleotides*, 1995, 14, 969–973.

Manoharan, M. et al., "Lipidic Nucleic Acids", *Terrchedron Letts.*, 1995, 36, 3651–3654.

Manoharan M. et al., "Cholic Acid–Oligonucliotide Conjugates for Antisense Applications", *Biorganic Med. Chem. Letts.*, 1994, 4, 1053–1060.

Manoharan, J. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan, M. et al., "Chemical Modifications to improve Uptake and Bioavailability of Antisense Oligonucleotides", *Annals NY Acad. Sciences*, 1992, 660, 306–309.

Martin, P., "Ein neuer Zugang zu 2'–O–Alkylribonucleosiden und Eigenschaften deren Oligonucleotide", *Helverica Chemica Acta*, 1994, 78, 486–504.

Mishra, R.K. et al., "Improved leishmauicidal effect of phosphorotioate antisense oligonucleotides by LDL–medicated delivery", *Biochim Et Biophysica*, 1995, 1264, 229–237.

Nielsen, P.E. et al., "Sequence–Selective Recognition of DNA by Strand Displacement with a Thymine–Substituted Polyamide", *Science*, 1991, 254, 1497–1500.

Oberhauser, b. et al., "Effective incorporation of 2'O–methyl–oligonucleotides into liposomes and enhanced cell association through modification with thiocholesterol", *Nucl. Acids Res.*, 1992, 20, 533–538.

Padmapriya, A.A. et al., "Large–Scale Synthesis, Purification, and Analysis of Oligodeoxynucleotide Phosphorothioates," *Antisense Res. Devel.*, 1994, 4, 185–199.

Paul, C.H. et al., "Acid Binding and derritylation during oligonucleotide synthesis, " *Nucl. Acids Res.*, 1996, 24(15), 3048–3052.

Saison–Bechmoaras, T. et al., "Short modified antisense oligonucleotides directed against Ha–*ras* point mutation induce selective cleavage of the mRNA and inhibit T24 cells proliferation", *EMBO J.*, 1991, 10, 1111–1118.

Sekine, M et al., "Sythesis and Properties of S,S–Diaryl Nucleoside Phosphorodithiotes in Oligonucleotide Synthesis", *J. Org. Chem.*, 1979, 44(19), 2325–2326.

Septak, M., "Kinetic studies on depurination and detritylation of CPG–bound intermediates during oligonucletide synthesis, " *Nucl. Acids Res.*, 1996, 24(15), 3053–3058.

Shea, R.G. et al., "Synthesis, hybridization properties and antiviral activity of lipid–oligodeoxynucletide conjugates", *Nucl. Acids Res., 1990,* 18. 3777–3783.

Svinarchuk, F.P. et al., "Inhibition of HIV proliferation in MT–4 cells by antisense oligonucleotide conjugated to lipophilic groups", *Biochimie, 1993,* 79, 49–54.

Wright, P. et al., "Large Scale Synthesis of Oligonucleotides via phosphoramidite Nucleosides and a High–Loaded Polystyrene Support", *Tetrahedron Letts., 1993, 34,* 3373–3376.

Yau, E.K. et al., "Synthesis of Dinucleoside and Dinucleotide Phosphorodithioates Via a Phosphotriester Approach", *Tetrahedron Letts., 1990,* 31(14), 1953–1956.

Agrawal, S. (ed.) *Protocols for Oligonucleotides and Analogs,* Humana Press, Totowa, NJ, 1993.

Eckstein, F. (ed.) *Oligonucleotide and Analogues, A Practical Approach,* IRL Press, New York, 1991.

* cited by examiner

METHODS FOR REMOVING DIMETHOXYTRITYL GROUPS FROM OLIGONUCLEOTIDES

CROSS REFERENCE TO RELATED APPLICATIONS

This application is a continuation of U.S. application Ser. No. 09/271,220, filed Mar. 17, 1999, now issued as U.S. Pat. No. 6,399,765, the contents of which is incorporated herein by reference in its entirety.

FIELD OF THE INVENTION

This invention relates to processes for oligonucleotide synthesis and purification. In particular, this invention relates to the removal of the 5'-terminal dimethoxytrityl sugar-protecting groups following oligonucleotide synthesis. This invention is amenable to the purification of oligonucleotides following large-scale synthesis.

BACKGROUND OF THE INVENTION

Oligonucleotides and their analogs are routinely used in many diagnostic and research applications, as probes, primers, linkers, adaptors and antisense oligonucleotides. Antisense oligonucleotides have been used routinely in research to study the functions of gene products, i.e. proteins, by modulating the expression thereof. These oligonucleotides are designed to bind in a specific fashion to a particular mRNA sequence by hybridization (i.e., oligonucleotides that are specifically hybridizable with a target mRNA). Such oligonucleotides and oligonucleotide analogs are intended to inhibit the activity of the selected mRNA by any of a number of mechanisms, i.e. to interfere with translation reactions by which proteins coded by the mRNA are produced or initiate RNase H degradation of the mRNA. The inhibition of the formation of the specific proteins that are coded for by the mRNA sequences allows the study of functions of certain genes.

The specificity of antisense oligonucleotides and their analogs are also used therapeutically. Their mechanism of action limits side effects while increasing specificity. Presently, there are numerous antisense oligonucleotides in clinical trials against a wide range of targets and diseases and recently the first antisense oligonucleotide was approved by the FDA for marketing.

Applications of oligonucleotides and oligonucleotide analogs as antisense agents for therapeutic purposes, diagnostic purposes, and research reagents often require that the oligonucleotides or oligonucleotide analogs be synthesized in large quantities. This is especially true for their use as commercially available pharmaceutical drugs. The large-scale synthesis and purification of oligonucleotides on an economic scale presents different challenges than those in synthesis of small amounts for research.

Synthesis of oligonucleotides can be accomplished using both solution phase and solid phase methods. A general review of solid-phase versus solution-phase oligonucleotide synthesis is given in the background section of Urdea, et al. U.S. Pat. No. 4,517,338, entitled "Multiple Reactor System And Method For Oligonucleotide Synthesis". Oligonucleotide synthesis via solution phase can be accomplished with several coupling mechanisms.

One such solution phase preparation utilizes phosphorus triesters. Yau, E. K., et al., *Tetrahedron Letters,* 1990, 31, 1953, report the use of phosphorous triesters to prepare thymidine dinucleoside and thymidine dinucleotide phosphorodithioates. However, solution phase chemistry requires purification after each internucleotide coupling, which is labor intensive and time consuming.

Further details of methods useful for preparing oligonucleotides may be found in Sekine, M., et. al., *J. Org. Chem.,* 1979, 44, 2325; Dahl, O., *Sulfur Reports,* 1991, 11, 167–192; Kresse, J., et al., *Nucleic Acids Res.,* 1975, 2, 1–9; Eckstein, F., *Ann. Rev. Biochem.,* 1985, 54, 367–402; and Yau, E. K. U.S. Pat. No. 5,210,264.

The current method of choice for the preparation of naturally occurring oligonucleotides, as well as oligonucleotides with modified internucleotide linkages such as phosphorothioate and phosphoro-dithioate oligonucleotides, is via solid-phase synthesis wherein an oligonucleotide is prepared on a polymer support (a solid support).

Solid-phase synthesis relies on sequential addition of nucleotides to one end of a growing oligonucleotide chain. Typically, the 3'-most nucleoside (having protecting groups on any exocyclic amine functionalities present) is attached to an appropriate solid support and activated phosphorus compounds (typically nucleotide phosphoramidites, also bearing appropriate protecting groups) are added stepwise in a 3' to 5' direction to elongate the growing oligonucleotide. The activated phosphorus compounds are reacted with the growing oligonucleotide using "fluidized bed" technology to mix the reagents. A number of solid-phase synthesizers are available commercially which automate this process.

A common requirement for oligonucleotide synthesis, whether by solution phase or solid phase methods, is protection of the 5'-OH group of the incoming nucleoside or nucleotide monomer. The internucleoside linkages are formed between the 3'-functional group of the incoming nucleoside and the 5'-OH group of the 5'-most nucleoside of the growing, support-bound oligonucleotide. Many methods of oligonucleotide synthesis require the phosphorylation or phosphitylation of the 3'-OH, and thus, a temporary protecting group is necessary on the 5'-OH (Gait, M. S., *Oligonucleotide Synthesis A Practical Approach,* IRL Press 1985, 1–22). A 5'-OH protecting group is desired to prevent dimerization of the incoming nucleosides. The 5'-OH protecting group needs to be very acid labile to prevent depurination of the oligonucleotide during removal of the protecting group. The most common agent is dimethoxytrityl (DMTr).

In practice, there are two steps where DMTr is required. During the stepwise synthesis of oligonucleotide, a DMTr protected monomer is added to the elongating chain. The trityl group is removed from the 5'-most nucleotide during a specific detritylation step, most often using a solution of a mild organic acid such as dichloracetic acid or trichloroacetic acid in an organic solvent (e.g. toluene or dichloromethane). After completion of oligonucleotide synthesis and cleavage from the solid support, the 5'-terminal DMTr group is kept on the oligonucleotide (referred to as a DMTr-on oligonucleotide) to facilitate separation from side reaction products which do not have DMTr. High performance liquid chromatography is often used for this purification step. After this initial purification, the final trityl needs to be removed giving a DMTr-off oligonucleotide. Due to the less stringent requirement for an anhydrous environment, a weak acid such as glacial acetic acid (or a dilute solution thereof) can be used for detritylation of the final product.

In a large-scale synthesis method described by Beaucage, S. (in Chapter 3 of *Protocols for Oligonucleotides and Analogs,* Agrawal, S. (Ed.), 1993, Humana Press, Totowa, N.J.), after reverse-phase HPLC purification, fractions containing the product of interest are pooled. The fractions containing oligonucleotide are typically in methanol and a salt. Triethylammonium acetate is the most common salt for small scale synthesis of oligonucleotides. The solvent is removed using rotary evaporation, leaving the DMTr-on oligonucleotide. The DMTr-on oligonucleotide is treated with 80% glacial acetic acid typically for 30 or 60 minutes. The oligonucleotide is then recovered by ethanol precipitation and applied to a PD-10 Sephadex® G-25 column to recover the sodium salt of the oligonucleotide. Alternatively, Padmiapriya, A. A., et al. (*Antisense Res. and Develop.,* 1994, 4, 185–199) describe the use of Dowex-50 in lieu of the G-25 column.

In another method, sodium acetate is used as the salt during HPLC, thereby forgoing the need for recovery of the sodium salt. In this method, glacial acetic acid is added directly to the pooled fractions. After reacting for 30 minutes, the oligonucleotide is ethanol precipitated, reconstituted in water and further reacted in glacial acetic acid several additional times to obtain complete removal of DMTr. Then, the oligonucleotide is subjected to a final ethanol precipitation to obtain the purified product.

During oligonucleotide detritylation, a fine balance between detritylation and depurination exists. Incubating the oligonucleotide in acid for too short of a time will results in incomplete detritylation, while too long of a time will result in increased depurination, thereby reducing yields and purity. In small-scale syntheses, the yield is not an important consideration, due to the small amounts required for typical uses. For the large-scale synthesis of oligonucleotides, each step needs to be optimized to achieve maximum yields.

In the art, it is recognized that optimizing deprotection during oligonucleotide synthesis is a significant problem. WO 96/03417 describes improved methods of detritylation during oligonucleotide synthesis. Paul, C. H., and Royappa, A. T. (*Nucleic Acids Res.,* 1996, 24, 3048–3052) and Septak, M. (*Nucleic Acids Res.,* 1996, 24, 3053–3058) also describes ways of optimizing detritylation during oligonucleotide synthesis.

Yet, optimization of deprotection post-oligonucleotide synthesis is often overlooked. If an attempt is made to achieve maximum post-synthesis deprotection, the incubation time for each oligonucleotide is determined empirically as deprotection rates are specific to an oligonucleotide sequence and particular reaction conditions.

Thus there is the need for improved methods to optimize deprotection of a acid-labile protecting group-containing oligonucleotide following synthesis.

SUMMARY OF THE INVENTION

Figure 1:
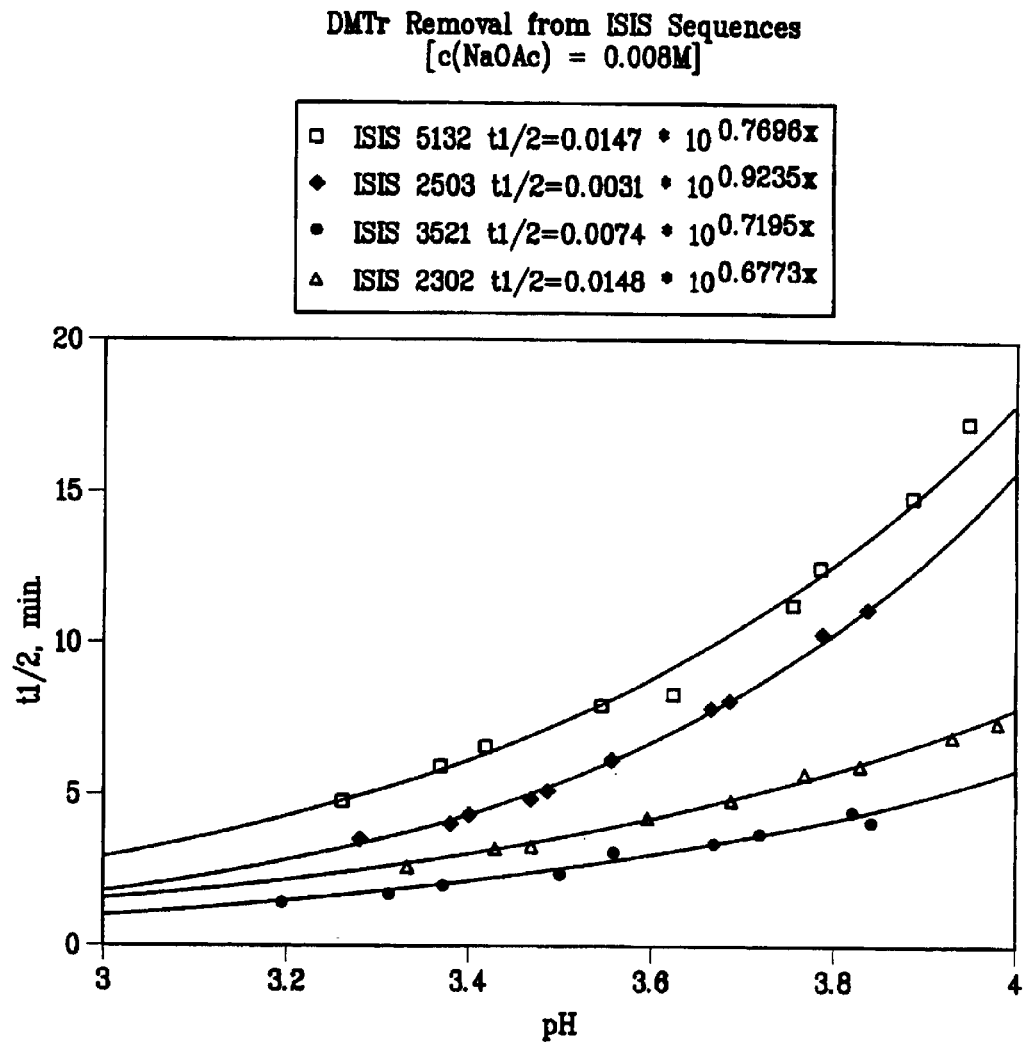
FIG. 1 depicts a plot of half-life versus pH for a series of oligonucleotides.

The invention described herein relates to methods for improving deprotection of an acid-labile 5'-OH protecting group-containing oligonucleotide. This method involves determining a half-life for the acid-labile 5'-OH protecting group-containing oligonucleotide in an acid solution capable of removing the protecting group from said oligonucleotide, and reacting the oligonucleotide in the acid solution for approximately 5–20 half-lives. In another embodiment the method further comprises purifying the protecting group-containing oligonucleotide prior to deprotection.

Preferred Embodiments

Methods for synthesizing oligonucleotides include conversion of a nucleoside or nucleobase (or an analog thereof) to an activated phosphorus compound followed by solution phase or solid phase chemistries to couple the activated phosphorus compound to a growing oligonucleotide chain. Solution and solid phase chemistries typically involve a multi-step reaction cycle which is repeated for each addition of the activated phosphorus compound. Representative solution phase techniques are described in U.S. Pat. Nos. 5,210,264 and 5,571,902, both herein incorporated by reference. Additional solution phase chemistries utilizing acid-labile protecting groups, such as di-p-methoxytrityl (DMTr), are described in Barber, I., et al. (*Antisense Res. and Devel.,* 1995, 5, 39–47) and Bonora, G. M., et al. (*Nucl. Acids Res.,* 1993, 21, 1213–1217).

Representative solid phase techniques are those typically employed for DNA and RNA synthesis utilizing standard phosphoramidite chemistry (see, e.g., *Protocols For Oligonucleotides And Analogs,* Agrawal, S., ed., Humana Press, Totowa, N.J., 1993). A typical solid-phase reaction cycle for using phosphoramidites wherein DMTr is the protecting group includes the following steps: washing the solid support (which contains the DMTr protected nucleoside or a growing oligonucleotide chain), detritylation (deprotection of the 5'-OH sugar protecting group), washing, coupling of a phosphoramidite monomer to the detritylated nucleoside, washing, capping of unreacted/uncoupled support bound phosphoramidite monomer, washing, oxidation of the phosphorus nucleoside linkage, and washing (*Oligonucleotides and Analogues A Practical Approach,* Eckstein, F. Ed., IRL Press, New York, 1991). In some methods, oxidation may follow capping. Post-synthesis treatment of crude oligonucleotide is similar for both solid-phase and solution phase synthesis.

In solid support synthesis, the deprotected 5'-OH of the support bound nucleoside, or growing oligomeric chain, is reacted with a 5'-protected activated phosphorus nucleoside to produce a covalent linkage therebetween. The activated phosphorus compound is one that is known to undergo a coupling reaction with the deprotected 5'-OH of a growing oligomeric chain according to standard synthetic methodologies, such as, for example, the phosphoramidite, phosphotriester and H-phosphonate synthetic methods. See for example Caruthers U.S. Pat. Nos. 4,415,732; 4,458,066; 4,500,707; 4,668,777; 4,973,679; and 5,132,418; Yau, E. K. U.S. Pat. No. 5,210,264; and Koster U.S. Pat. Nos. 4,725,677 and Re. 34,069; each of the disclosures of which are hereby incorporated by reference in their entirety, Sekine, M., et. al., *J Org. Chem.,* 1979, 44, 2325; Dahl, O., *Sulfur Reports,* 1991, 11, 167–192; Kresse, J., et al., *Nucleic Acids Res.,* 1975, 2, 1–9; Eckstein, F., *Ann. Rev. Biochem.,* 1985, 54, 367–402; and *Oligonucleotides and Analogues A Practical Approach,* Eckstein, F. Ed., IRL Press, New York, 1991.

The most common 5'-OH protecting groups are substituted trityl groups (see, in general, Beaucage, S. and Iyer, R. P., Tetrahedron, 1992, 48, 2223–2311). The most commonly used is di-p-methoxytrityl (DMTr). Other substituted trityl groups include monomethoxytrityl group and 4, 4', 4"-tris-(4,5-dichlorophthalimido) trityl group. Further substitutions are within the scope of those skilled in the art. Lipophilic trityl groups can used be used to aid in the purification of the oligonucleotide by reverse-phase HPLC. Non-trityl groups that are amenable to the present invention include p-phenylazophenyloxycarbonyl group (PAPoc), 9-fluorenylmethoxycarbonyl (Fmoc) group, 2,4-dinitrophenylethoxycarbonyl group (DNPEoc). 4-(methylthiomethoxy)butyryl (MTMB), 2-(methylthiomethoxymethyl)benzoyl (MTMT), and 2-(isopropylthiomethoxymethyl)benzoyl (PTMT).

Following completion of oligonucleotide synthesis, the oligonucleotide is cleaved from the support using ammonium hydroxide and further purified. The resulting oligonucleotide has a DMTr group to facilitate separation from deletion sequences, most commonly n−1 sequences. Purification of the oligonucleotide is typically accomplished by the use of reverse-phase high performance liquid chromatography. Other methods of purification are contemplated by the present invention, including strong ion exchange chromatography, and are routine in the art. The appropriate solvents used in these methods of purification are also routine in the art. These solvents may contain inorganic salts to facilitate purification. In a preferred embodiment, sodium acetate is used. If other inorganic salts are used, an additional step may be required to isolate the sodium salt of the oligonucleotide. Once the full-length oligonucleotide containing DMTr groups is isolated, the DMTr groups need to be removed with a deprotecting agent.

Deprotecting agents are those agents used to remove the 5'-OH protecting group (see, in general, Beaucage, S. and Iyer, R. P., Tetrahedron, 1992, 48, 2223–2311). Mild acids are used to allow detritylation to occur while minimizing depurination. The most commonly used agent for DMTr removal is glacial acetic acid. Mild Lewis acids such as zinc bromide or boron trifluoride etherate could also be used for deprotection. Use of protecting groups other than substituted trityl groups may require different deprotecting agents, and are known in the art (see, in general, Beaucage, S. and Iyer, R. P., Tetrahedron, 1992, 48, 2223–2311).

In order to maximize yields and purity, an optimum deprotection time is determined. This optimum time considers, for example, both the detritylation reaction and depurination side-reaction for a DMTr-on oligonucleotide and attempts to achieve a desired balance between the two. As disclosed in this invention, the rate of deprotection varies for each oligonucleotide sequence based on factors including sequence composition, oligonucleotide concentration, salt concentration, organic solvent composition and pH. A half-life for the DMTr-on oligonucleotide under the detritylation reaction conditions is determined and the desired level of purity is achieved by reacting the DMTr-on oligonucleotide in the deprotecting agent for a specified number of half-lives. The desired level of purity is represented, in percent, by $[1-(0.5)^n]*100$ where n=number of half-lives. Some representative numbers of half-lives and purity are shown in Table 1. The protected oligonucleotides are reacted for approximately 5 to 20 half-lives. In a preferred embodiment, the protected oligonucleotide is reacted for approximately 10 to 15 half-lives.

TABLE 1

Exponential decay of DMTr-on oligonucleotide

| No. of half-lives | % DMTr-off oligonucleotide |
| --- | --- |
| 5 | 96.8750 |
| 8 | 99.6094 |

TABLE 1-continued

Exponential decay of DMTr-on oligonucleotide

| No. of half-lives | % DMTr-off oligonucleotide |
| --- | --- |
| 10 | 99.9023 |
| 12 | 99.9756 |
| 15 | 99.9969 |
| 18 | 99.9996 |

Several analytical methods are available for use in the determination of the half-life of the protect oligonucleotide. These methods include reverse-phase HPLC (RP-HPLC), strong anion exchange (SAX) chromatography, capillary gel electrophoresis, and other types of gel electrophoresis, all of which are well known in the art. These methods are used to determine the ratio of protecting group-on oligonucleotide to protecting group-off. The half-life is defined as the time when 50% of the oligonucleotide is converted from protecting group-on to protecting group-off. An alternative approach is the determination of the released protecting group-alcohol (e.g., DMTr-OH) by HPLC. Spectroscopic methods, including quantitative mass spectrometry and nuclear mass resonance (NMR) can also be used.

According to one embodiment of the present invention, the half-life is determined experimentally. Samples are removed periodically and analyzed by any of the above methods to determine the percentage of protecting group-on oligonucleotide present. This percentage is plotted versus time and the point where the time intersects 50% is the half-life.

In another embodiment of the present invention, a standard curve is generated by plotting half-lives vs. pH wherein half-lives are determined over a range of pH values. The half-lives of the curve are determined experimentally as described above or by evaluating exponential decay of the protecting group-on oligonucleotide using standard exponential decay equations. Then, while the deprotection reaction is occurring, the pH can be monitored and a half-life determined based on the standard curve.

In another embodiment of the present invention, it is possible to make a determination of the half-life from a single determination. If no standard curves are desired, perhaps because of the large number of different sequences synthesized, a sample of the deprotection reaction can be removed for analysis of the ratio of protecting group-on and protecting group-off oligonucleotide. The standard exponential decay equation can be used to determine the half-life and the reaction continued for the desired number of half-lives.

Solid phase synthesis uses a wide variety of solid supports, any of which is amenable to the present invention. Solid supports used in solid-phase oligonucleotide synthesis include controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, et al., *Tetrahedron Letters* 1993, 34, 3373), Poros—a copolymer of polystyrene/divinylbenzene or PRIMER SUPPORT® HL, 30 —a polystyrene based support (Pharmacia Biotech, Piscataway, N.J.). Many other solid supports are commercially available and also amenable to the present invention.

It is well known to use similar techniques to prepare oligonucleotides incorporating phosphorothioate linkages and oligonucleotides incorporating 2'-alkoxy or 2'-alkoxyalkoxy modifications, including 2'-O- methoxyethyl (Martin, P., Helv. Chim. Acta 1995, 78, 486). It is also well known to use similar techniques and commercially available modified phosphoramidites such as biotin, fluorescein, acridine or psoralen-modified phosphoramidites (available from Glen Research, Sterling, Va.) to synthesize fluorescently labeled, biotinylated or other conjugated oligonucleotides.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

Specific examples of preferred modified oligonucleotides include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates (abbreviated as P=S) and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester (abbreviated as P=O) backbone is represented as O—P—O—$CH_2$. Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science* 1991, 254, 1497; U.S. Pat. No. 5,539,082). Other preferred modified oligonucleotides may contain one or more substituted sugar moieties comprising one of the following at the 2' position: OH, SH, $SCH_3$, F, OCN, $OCH_3OCH_3$, $OCH_3O(CH_2)$, $CH_3$, $O(CH_2)_nNH_2$ or $O(CH_2)_n\ _{CH3}$ where n is from 1 to about 10; O—R or O—R—O—R where R is $C_1$ to $C_{10}$ lower alkyl, substituted lower alkyl, alkaryl or aralkyl; 0-substituted lower alkyl, Cl; Br; CN; $CF_3$; $OCF_3$; O—, S—, or N—alkyl; O—, S—, or N—alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'—O—methoxyethyl [which can be written as 2'—O—$CH_2CH_2OCH_3$, and is also known as 2'—O—(2-methoxyethyl) or 2'-methoxyethoxy] (Martin et al., *Helv. Chim. Acta* 1995, 78, 486). Other preferred modifications include 2'-methoxy (2'-O-$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of the 5' terminal nucleotide. Oligonucleotides may also have sugar mimetics such as cyclobutyls in place of the pentofuranosyl group.

The oligonucleotides made by the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine and 5-methylcytosine, as well as synthetic nucleobases, e.g., 5-bromouracil, 5-hydroxymethyluracil, 8-azaguanine, 7-deazaguanine, $N^6$(6-aminohexyl) adenine and 2,6-diaminopurine (Kornberg, A., DNA Replication, W. H. Freeman & Co., San Francisco, 1974, pp. 75–77; Gebeyehu, G., et al., *Nucleic Acids Res.* 1987, 15, 4513). 5-methylcytosine (5-me-C) is presently a preferred nucleobase, particularly in combination with 2'-O-methoxyethyl modifications.

Another preferred additional or alternative modification of the oligonucleotides prepared according to the methods of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine nucleobase may also be utilized to link a lipophilic moiety to an oligonucleotide of the invention (Gebeyehu, G., et al., *Nucleic Acids Res.* 1987, 15, 4513). Such lipophilic moieties include but are not limited to a cholesteryl moiety (Letsinger et al, *Proc. Natl. Acad. Sci. USA* 1989, 86, 6553), cholic acid (Manoharan et al., *Bioorg. Med. Chem. Let.* 1994, 4, 1053), a thioether, e.g., hexyl-S-tritylthiol (Manoharan et al., *Ann. N.Y. Acad. Sci.* 1992, 660, 306; Manoharan et al., *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al., *EMBO J.* 1991, 10, 111; Kabanov et al., *FEBS Lett.* 1990, 259, 327; Svinarchuk et al., *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995 36, 3651; Shea et al, *Nucl. Acids Res.* 1990, 18, 3777), a polyamine or a polyethylene glycol chain (Manoharan et al., *Nucleosides & Nucleotides* 1995, 14, 969), or adamantane acetic acid (Manoharan et al., *Tetrahedron Lett.* 1995, 36, 3651), a palmityl moiety (Mishra et al, *Biochim. Biophys. Acta* 1995, 1264, 229), or an octadecylamine or hexylamino-carbonyl-oxycholesterol moiety (Crooke et al., *J Pharmacol. Exp. Ther.* 1996, 277, 923). Oligonucleotides comprising lipophilic moieties, and methods for preparing such oligonucleotides, as disclosed in U.S. Pat. No. 5,138,045, No. 5,218,105 and No. 5,459,255, the contents of which are hereby incorporated by reference.

Oligonucleotides which are chimeric oligonucleotides may also be prepared according to the methods of the present invention. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g., 2'-fluoro- or 2'-O-methoxyethyl-substituted). Other chimeras include "wingmers," also known as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—$CH_2CH_2OCH_3$) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides of the invention may bear a 2'-O-methoxyethyl (—O—$CH_2CH_2OCH_3$) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2'-O-methoxyethyl modifications, oligonucleotides containing other modifications which enhance antisense efficacy, potency or target affinity are also preferred. Chimeric oligonucleotides comprising one or more such modifications are presently preferred. Oligonucleotides prepared in accordance with the methods of this invention are from 5 to 50 nucleotides in length. In the context of this invention it is understood that this encompasses non-naturally occurring oligomers as hereinbefore described, having from 5 to 50 monomers.

EXAMPLES

Example 1

Synthesis of Oligonucleotides

Unmodified oligodeoxynucleotides were synthesized on an automated DNA synthesizer (Pharmacia OligoPilot) using standard phosphoramidite chemistry. β-cyanoethyldiisopropyl-phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one 1,1-dioxide in acetonitrile for the stepwise thiation of the phosphite linkages. The thiation cycle wait step was increased to 68 seconds and was followed by the capping step.

After cleavage from the Primer Support® HL, 30 Support (Pharmacia) and deblocking in concentrated ammonium hydroxide at 55° C. for 18 hours, the oligonucleotides were isolated by precipitation twice out of 0.2 M NaOAc with 3.5 volumes ethanol and then further purified by reverse phase HPLC, as described by Chiang et al. (*J. Biol. Chem.* 1991, 266, 18162). HPLC fractions containing the DMTr-on oligonucleotide were pooled for further work-up.

The oligonucleotide sequences synthesized are listed in Table 2. All are fully phosphorothioated oligodeoxynucleotides and are shown 5' to 3'.

TABLE 2

Oligodeoxynucleotide sequences

| ISIS No. | SEQ ID NO. | Sequence | Target |
|---|---|---|---|
| 2302 | 1 | GCCCAAGCTGGCATCCGTCA | ICAM-1 |
| 2503 | 2 | TCCGTCATCGCTCCTCAGGG | Ha-Ras |
| 3521 | 3 | GTTCTCGCTGGTGAGTTTCA | PKC-a |
| 5132 | 4 | TCCCGCCTGTGACATGCATT | C-raf-1 |

Example 2

General Method for Determination of $t_{1/2}$ for DMTr-Removal From Oligonucleotides In a typical experiment a solution of DMTr-on oligonucleotide (200 ml, c=1750 OD/ml) was treated with an acidic buffer (700 ml). Buffer solutions consisted of aqueous NaOAc (0.01M) solutions titrated to pH 2.70, 2.79, 2.87, 2.95, 3.00, 3.06, 3.17, 3.21, 3.31 and 3.37, respectively. At different time points (t) samples (20 ml) were taken and added into NaOH (1M, 0.5 ml) to stop the DMTr-removal reaction. This solution (15 ml) was analyzed by RP-HPLC. Peak areas for DMTr-on and DMTr-off oligo were added and set to 100%. The percentage of DMTr-on oligo was determined and put into the following equation:

$$\ln(0.5)/\ln(\%DMTr\text{-}on/100) \times t = t_{1/2}$$

Typically, three time points were taken and the average $t_{1/2}$ was determined.

The pH of each reaction mixture was measured. The half-life times were plotted over the pH and analytical equations that fit the data were determined using Cricket Graph charting software. FIG. 1 shows the graphs determined for ISIS 5132, ISIS 2302, ISIS 2503 and ISIS 3521. At pH=3.6, the half-lives for ISIS 5132, 2503, 2302, and 3521 were 8.7 min, 6.5 min., 4.1 min., and 2.9 min., respectively.

The following equations for calculation of the half-life time of DMTr removal at a certain pH using an aqueous NaOAc buffer (0.01 M) were determined (x=pH):

ISIS 5132: $t_{1/2}=0.0147*10^{0.7696x}$

ISIS 2503: $t_{1/2}=0.0031*10^{0.9235x}$

ISIS 3521: $t_{1/2}=0.0074*10^{0.7195x}$

ISIS 2302: $t_{1/2}=0.0148*10^{0.6773x}$

Example 3

Procedure for DMTr Removal From Oligonucleotides

Crude oligonucleotide product was purified by RP-HPLC. DMTr-on fractions (15 l, ca $6\times10^6$ OD) were pooled and precipitated with ethanol (45 l) at <-20° C. The precipitate is isolated by centrifugation and reconstituted in water (c=1750 OD/ml). At room temperature, aqueous NaOAc solution (0.01 M, adjusted to pH 3.00 with glacial acetic acid, 12 l) is added and the mixture is stirred. After 5–10 min a sample (ca 5 ml) is removed from the vessel and the pH is measured using a pH meter. The half-life time is determined using the above equation and multiplied by 15 to give the total reaction time:

Examples

ISIS 5132: pH 3.53: $t_{1/2}$=7.66 min, reaction time: 115 min.
ISIS 3521: pH 3.65: $t_{1/2}$=3.13 min, reaction time: 47 min.
ISIS 2503: pH 3.68: $t_{1/2}$=7.76 min, reaction time: 116 min.
ISIS 2302: pH 3.68: $t_{1/2}$=4.60 min, reaction time: 69 min.

After the reaction is complete, NaOAc (3.0 M, pH=7.2, 0.54 l) is added, followed by cold ethanol (75 l, -20° C.). The precipitate is isolated by centrifugation and reconstituted in water.

Figure 2:
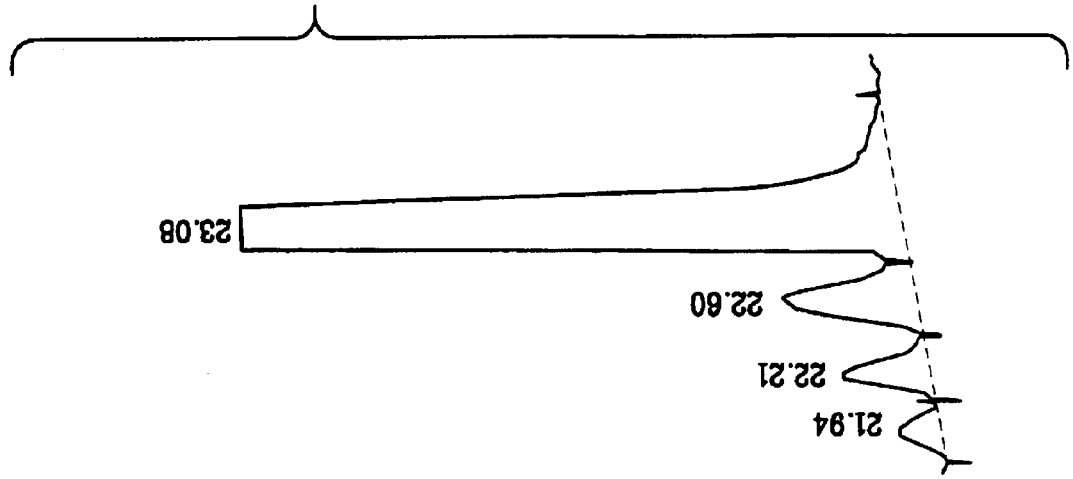
FIG. 2 depicts capillary gel electrophoresis (CGE) analysis of purified oligonucleotides detritylated for fifteen half-lives.
Figure 2:
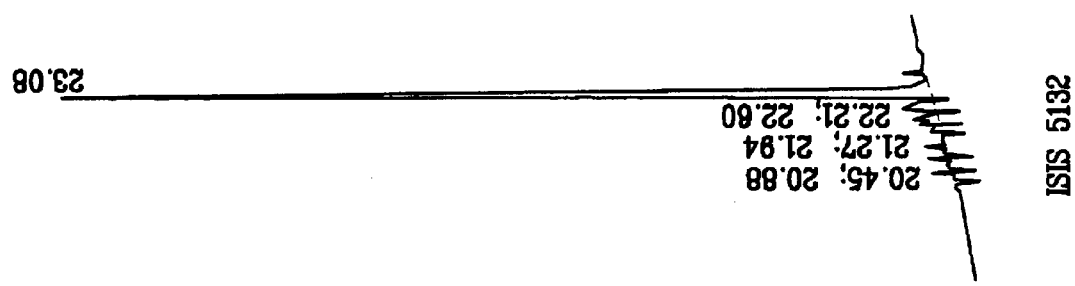
Figure 2:
Figure 2:

FIG. 2 shows CGE analysis of the purified oligonucleotides.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

---

What is claimed is:

1. A method for improving deprotection of an acid-labile 5'-OH protecting group-containing oligonucleotide comprising:

determining the half-life for said acid-labile 5'-OH protecting group-containing oligonucleotide in an acid solution capable of removing the acid-labile 5'-OH protecting group from said oligonucleotide, and reacting said acid-labile 5'-OH protecting group-containing oligonucleotide in said acid solution for approximately 5 to approximately 20 half-lives;

wherein said acid solution comprises acetic acid, dichloracetic acid, trichloroacetic acid, zinc bromide or boron trifluoride etherate.

2. The method of claim 1 wherein said oligonucleotide is reacted in said acid solution for approximately 10 to approximately 15 half-lives.

3. The method of claim 2 wherein said half-life is determined from a standard curve of pH values vs. half-lives.

4. The method of claim 2 wherein said half-life is determined by evaluating exponential decay of said protecting group-containing oligonucleotide.

5. The method of claim 2 wherein said deprotection is detritylation and said acid-labile 5'-OH protecting group is a trityl group.

6. The method of claim 4 wherein said trityl group is di-p-methoxytrityl.

7. A method for deprotecting an acid-labile 5'-OH protecting group-containing oligonucleotide comprising:

purifying said acid-labile 5'-OH protecting group-containing oligonucleotide, determining a half-life for said acid-labile 5'-OH protecting group-containing oligonucleotide in an acid solution capable of removing the acid-labile 5'-OH protecting group from said oligonucleotide, and reacting said acid-labile 5'-OH protecting group-containing oligonucleotide in said acid solution for approximately 10 to approximately 15 half-lives;

wherein said acid solution comprises acetic acid, dichloracetic acid, trichloroacetic acid, zinc bromide or boron trifluoride etherate.

8. The method of claim 7 wherein said purifying is done by high performance liquid chromatography or strong ion exchange chromatography.

9. The method of claim 7 wherein a solvent used in said high performance liquid chromatography contains sodium acetate.

10. The method of claim 7 wherein said half-life is determined from a standard curve of pH values vs. half-lives.

11. The method of claim 7 wherein said half-life is determined by evaluating exponential decay of said protecting group-containing oligonucleotide.

12. The method of claim 7 wherein said deprotection is detritylation and said acid-labile 5'-OH protecting group is a trityl group.

13. The method of claim 12 wherein said trityl group is di-p-methoxytrityl.

14. The method of claim 1 wherein said acid solution comprises acetic acid, dichloracetic acid, or trichloroacetic acid.

15. The method of claim 1 wherein said acid solution comprises dichloracetic acid.

16. The method of claim 7 wherein said acid solution comprises acetic acid, dichloracetic acid, or trichloroacetic acid.

17. The method of claim 7 wherein said acid solution comprises dichloracetic acid.

* * * * *

UNITED STATES PATENT AND TRADEMARK OFFICE
CERTIFICATE OF CORRECTION

PATENT NO. : 6,794,502 B2
DATED : September 21, 2004
INVENTOR(S) : Achim H. Krotz et al.

It is certified that error appears in the above-identified patent and that said Letters Patent is hereby corrected as shown below:

Title page,
Item [56], References Cited, OTHER PUBLICATIONS, "Barber" reference, please delete "phosphouiester" and insert therefor -- phosphotriester --;
"Chiang" reference, please delete "Olignucleotides" and insert therefor
-- Oligonucleotides --; and please delete "Molecul3" and insert therefor -- Molecule --;
"Dahl" reference, please delete "Phosphorodithioataes" and insert therefor
-- Phosphorodithioates --;
"Eck stein" reference, please delete "Eck stein" and insert therefor -- Eckstein --;
"Gait" reference, please delete "Modem" and insert therefor -- Modern --;
"Gebeyehu" reference, please delete "lolorimetric" and insert therefor -- colorimetric --.

Signed and Sealed this

Fourth Day of October, 2005

JON W. DUDAS
*Director of the United States Patent and Trademark Office*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: antisense sequence

<400> SEQUENCE: 1
gcccaagctg gcatccgtca                                              20

<210> SEQ ID NO 2
<211> LENGTH: 20
<212> TYPE: DNA
<213> ORGANISM: Artificial Sequence
<220> FEATURE:
<223> OTHER INFORMATION: antisense sequence

<400> SEQUENCE: 2
tccgtcatcg ctcctcaggg                                              20

<210> SEQ ID NO 3
<211> LENGTH: 20
<212> TYPE: DNA
<213> ORGANISM: Artificial Sequence
<220> FEATURE:
<223> OTHER INFORMATION: antisense sequence

<400> SEQUENCE: 3
gttctcgctg gtgagtttca                                              20

<210> SEQ ID NO 4
<211> LENGTH: 20
<212> TYPE: DNA
<213> ORGANISM: Artificial Sequence
<220> FEATURE:
<223> OTHER INFORMATION: antisense sequence

<400> SEQUENCE: 4
tcccgcctgt gacatgcatt                                              20
```